United States Patent [19]

Riondel

[11] Patent Number: 5,596,126
[45] Date of Patent: Jan. 21, 1997

[54] CATALYTIC PREPARATION OF SEC-BUTYL ACRYLATE

[75] Inventor: Alain Riondel, Forbach, France

[73] Assignee: Elf Atochem S.A., France

[21] Appl. No.: 422,957

[22] Filed: Apr. 17, 1995

[30] Foreign Application Priority Data

Apr. 15, 1994 [FR] France ................... 94 04525

[51] Int. Cl.⁶ ................................... C07C 69/52
[52] U.S. Cl. ................................... 560/205
[58] Field of Search ........................... 560/205

[56] References Cited

U.S. PATENT DOCUMENTS

| | | | |
|---|---|---|---|
| 3,037,052 | 5/1962 | Bortnick | 260/485 |
| 4,868,343 | 9/1989 | King et al. | 568/697 |
| 5,008,468 | 4/1991 | King et al. | 568/697 |
| 5,138,092 | 8/1992 | Pascual et al. | 560/205 |

FOREIGN PATENT DOCUMENTS

| | | |
|---|---|---|
| 612826 | 8/1994 | European Pat. Off. . |
| 677506 | 10/1995 | European Pat. Off. . |
| 7-125447 | 5/1995 | Japan . |

*Primary Examiner*—Paul J. Killos
*Attorney, Agent, or Firm*—Millen, White, Zelano, & Branigan, P.C.

[57] ABSTRACT

For preparing sec-butyl acrylate, acrylic acid is reacted with 1-butene in the presence of a zirconium-based solid superacid as the catalyst, for example a calcined reaction product of 10–15 parts by weight of ammonium sulphate and 100 parts by weight of zirconium hydroxide.

8 Claims, No Drawings

CATALYTIC PREPARATION OF SEC-BUTYL ACRYLATE

BACKGROUND OF THE INVENTION

The present invention relates to processes for preparing sec-butyl acrylate by reacting acrylic acid with 1-butene, 2-butene or a mixture thereof in the 5 presence of an acid catalyst.

Processes of this type are already known, these processes using as the catalyst an acidic ion exchange resin containing sulphonic acid groups (U.S. Pat. No. 3,037,052), methane-sulphonic acid (Brazilian Patent -78 022 55), an ion exchange resin containing sulphonic acid groups (EP-A-445 859) which is of improved texture and a caesium, rubidium, thallium, ammonium or potassium silicotungstate (JP-A-4, 139,148).

SUMMARY OF THE INVENTION

A catalyst has now been found which gives a better selectivity towards butyl acrylate than all of the known catalysts and which represents the best activity/selectivity compromise.

The subject of the invention is thus a process for preparing sec-butyl acrylate of the formula:

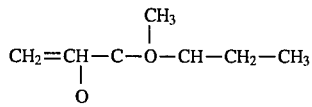

by reacting acrylic acid of the formula

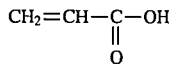

with 1-butene of the formula

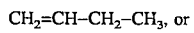

2-butene of the formula

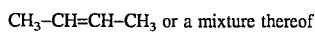

in the presence of a catalytic amount of an acid catalyst, wherein the catalyst is a zirconium-based solid superacid. (A "superacid" is defined herein as a product having an acidity higher than that of a solution of 100% sulfuric acid).

The reaction may be carried out between 50° and 120° C. at a pressure of 5 to 30 bar with a reaction time of 0.5 to 6 hours and with a 0.3 to 10 butene-to-acrylic acid molar ratio and in the presence of a stabilizing agent such as, for example, hydroquinone methyl ether, phenothiazine, hydroquinone and mixtures thereof in all proportions, which is used in an amount between 150 and 3000 ppm relative to the acrylic acid.

The product of reaction of zirconium hydroxide and ammonium sulphate may especially be used as the catalyst, the percentage range by weight of ammonium sulfate relative to zirconium hydroxide being preferably about 10% to at least 15% and especially about 15% At lower than 10% there is generally observed a decreased activity of the catalyst, and at higher than 15%, there is generally no beneficial effect on the activity as compared to 15%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius and unless otherwise indicated, all parts and percentages are by weight.

The entire disclosures of all applications, patents and publications, cited above and below, and of corresponding French application 9404525, are hereby incorporated by reference.

EXAMPLES

Example 1

Preparation of a zirconium-based solid super-acid

I. Preparation of $Zr(OH)_4$ 88 g of $ZrOCl_2$ octahydrate are dissolved at room temperature in 800 ml of water in a 1-liter jacketed reactor fitted with:
  a mechanical stirrer,
  a temperature probe,
  a pH probe.

About 50 ml of 25 % $NH_4OH$ are introduced slowly, at room temperature, such that the pH of the final solution is basic and between 8 and 9.

The white precipitate of $Zr(OH)_4$ obtained is then:

1) Washed with water to remove the chloride ions,
2) Oven-dried overnight at 100° C. under reduced pressure.

About 40 g of dry $Zr(OH)_4$ are thus obtained.

II. Sulphation—calcination $Zr(OH)_4$ and $NH_4(SO_4)_2$ (15% by weight relative to $Zr(OH)_4$) are mixed together using a grinder.

The solid obtained is then calcined in dry air at 650° C., to form $ZrO-SO_4$ bonds.

After cooling, a white solid is obtained, which is designated as ZrSA15.

Example 2

Preparation of sec-butyl acrylate 0.9 mol (51 g) of liquid 1-butene, one mole (72 g) of acrylic acid, 11 g (8.5 % by weight/charge) of ZrSA15 and 0.018 g (250 ppm relative to the acrylic acid) of hydroquinone methyl ether, which serves as a stabilizing agent, are charged at room temperature into a stainless steel reactor with a capacity of 200 ml, fitted with a thermometer and a manometer. The reactor is closed and is immersed in an oil bath at 150° C. The reaction medium is maintained at 100° C. with stirring for four hours. The pressure falls from 10 bar at the start of the reaction to 4 bar at the end of the reaction. At the end of the reaction, the reaction mixture is cooled to room temperature. The reactor is then opened so as to degas the unreacted butene.

The product obtained is subjected to the following analyses:
  potentiometry,
  gas chromatography.

The conversion of the acrylic acid is thus determined by potentiometric assay: the conversion of the 1-butene is determined from the mass of 1-butene degassed and from the residual 1-butene dissolved in the medium by gas chromatography, and the yield of sec-butyl acrylate is determined by a gas chromatographic assay.

These values make it possible to ascertain the selectivity towards sec-butyl acrylate relative to the acrylic acid and relative to the 1-butene. The results obtained are collated in Tables 1 and 2.

Example 3 (comparative)

Example 2 is repeated, except that the catalyst is replaced by an acidic resin containing sulphonic groups, Amberlyst 15 sold by Rohm and Haas.

The results obtained are tabulated in Tables 1 and 2.

Examples 4 and 5 (comparative)

Example 2 is repeated, except that the catalyst is replaced by other acidic catalysts, $H_3PW_{12}O_{40}$ and $Cs_3PW_{12}O_{40}$ respectively.

The results obtained are tabulated in Tables 1 and 2.

TABLE 1

| | | Gas chromatographic analysis (%) of the crude reaction mixtures obtained | | | | | | | |
|---|---|---|---|---|---|---|---|---|---|
| Example | Catalyst | C4 | 2-BUOH | C8 | AA(a) | 2BUA | Dimer | AC8 | AC12 |
| 2 | ZrSA 15 | 10.4 | 0.25 | 1.8 | 27.5 | 57 | 1.3 | 0.13 | 0.16 |
| 3 | A 15 | 7.6 | 0.4 | 2.6 | 25.6 | 57.4 | 3.2 | 0.16 | 0.5 |
| 4 | $H_3PW_{12}O_{40}$ | 6.9 | 0.5 | 3.6 | 28.3 | 48.3 | 1.8 | 0.25 | 2.8 |
| 5 | $CsPW_{12}O_{40}$ | 9.8 | 0.58 | 4 | 26.6 | 53.4 | 2.27 | 0.21 | 2.1 |

(a) Potentiometric assay
C4: Butene
2-BUOH: sec-Butanol
C8: Dibutene
A C8: C8 Acrylate
A C12: C12 Acrylate

TABLE 2

| | Synthesis of 2-BUA - Results | | | | | |
|---|---|---|---|---|---|---|
| Example | Material balance % | CAA (%) | CC4 (%) | Y 2-BUA (%) | S/C4 (%) | S/AA (%) |
| 2 | 97.7 | 60 | 63 | 59 | 93.6 | 98.3 |
| 3 | 98 | 67 | 80 | 61.5 | 76.2 | 91.8 |
| 4 | 100 | 53 | 80 | 52 | 65 | 99.6 |
| 5 | 100 | 56 | 78 | 53 | 68 | 94.6 |

C: conversion
Y: yield
S: selectivity

The activities of the catalysts tested are classified in the following order:

Amberlyst=Zr SA 15 (OP 135)>$CS_3PW_{12}O_{40}$, $H_3PW_{12}O_{40}$

In terms of selectivity towards 2-BUA/C4, the order becomes:

ZrSA15>Amberlyst>$Cs_3PW_{12}O_{40}$, $H_3PW_{12}O_{40}$

It thus concluded from these tests that the best activity/selectivity compromise is represented by the use of ZrSA15.

The preceding examples can be repeated with similar success by substituting the generically or specifically described reactangs and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing sec-butyl acrylate of the formula $$CH_2=CH-\underset{\underset{O}{\|}}{C}-O-\underset{\underset{CH_3}{|}}{CH}-CH_2-CH_3$$

comprising reacting acrylic acid of the formula $$CH_2=CH-\underset{\underset{O}{\|}}{C}-OH$$

with 1-butene of the formula $$CH_2=CH-CH_2-CH_3$$

2-butene of the formula $$CH_3-CH=CH-CH_3 \text{ or a mixture thereof}$$

in the presence of a catalytic amount of an acid catalyst, the improvement wherein said catalyst consists essentially of a zirconium-based solid superacid.

2. A process according to claim 1, said process being conducted between 50° and 120° C. at a pressure of 5 to 30 bar with a reaction time of 0.5 to 6 hours and with a 0.3 to 10 butene-to acrylic acid molar ratio and in the presence of a stabilizing agent selected from the group consisting of hydroquinone methyl ether, phenothiazine, hydroquinone and mixtures thereof in all proportions in an amount between 150 and 3000 ppm relative to the acrylic acid.

3. A process according to claim 1, wherein the catalyst is a calcined reaction product of zirconium hydroxide and ammonium sulphate.

4. A process according to claim 2, wherein the catalyst is the reaction product of zirconium hydroxide and ammonium sulphate.

5. A process according to claim 3, wherein the percentage range by weight of ammonium sulphate to zirconium hydroxide is about 10 to at least about 15%.

6. A process according to claim 4, wherein the percentage range by weight of ammonium sulphate to zirconium hydroxide is about 10 to at least about 15%.

7. A process according to claim 3, wherein the ammonium sulphate constitution is 15% by weight of the zirconium hydroxide.

8. A process according to claim 4, wherein the ammonium sulphate constitution is 15% by weight of the zirconium hydroxide.

* * * * *